US00PP32876P2

(12) United States Plant Patent
Mowrey et al.

(10) Patent No.: US PP32,876 P2
(45) Date of Patent: Mar. 9, 2021

(54) BLUEBERRY PLANT NAMED 'DRISBLUETWENTYTHREE'

(50) Latin Name: ***Vaccinium corymbosum* L.**
Varietal Denomination: DrisBlueTwentyThree

(71) Applicant: Driscoll's, Inc., Watsonville, CA (US)

(72) Inventors: Bruce D. Mowrey, Watsonville, CA (US); Esther Kibbe, Watsonville, CA (US); Marta C. Baptista, Watsonville, CA (US); Raymond L. Jacobs, III, Watsonville, CA (US); Sarah Wool, Watsonville, CA (US); James Olmstead, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 16/873,113

(22) Filed: Feb. 3, 2020

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./157
See application file for complete search history.

(56) References Cited

U.S. PATENT DOCUMENTS

| | | | |
|---|---|---|---|
| PP6,699 | P | 3/1989 | Wood |
| PP11,807 | P2 | 3/2001 | Lyrene |
| PP12,783 | P2 | 7/2002 | Lyrene |
| PP15,146 | P3 | 9/2004 | Hancock |
| PP19,503 | P3 | 11/2008 | Lyrene |
| PP20,436 | P2 | 10/2009 | Caster et al. |
| PP20,449 | P2 | 11/2009 | Caster et al. |
| PP20,488 | P2 | 11/2009 | Caster et al. |
| PP24,407 | P3 | 4/2014 | Caster et al. |
| PP24,489 | P3 | 5/2014 | Caster et al. |
| PP24,568 | P3 | 6/2014 | Caster et al. |
| PP24,569 | P3 | 6/2014 | Caster et al. |
| PP24,605 | P3 | 7/2014 | Caster et al. |
| PP26,287 | P3 | 1/2016 | Caster et al. |
| PP26,451 | P3 | 3/2016 | Caster et al. |
| PP26,537 | P3 | 3/2016 | Caster et al. |
| PP26,643 | P3 | 4/2016 | Caster et al. |
| PP26,748 | P3 | 5/2016 | Caster et al. |
| PP27,622 | P3 | 1/2017 | Caster et al. |
| PP28,933 | P2 | 2/2018 | Caster et al. |

OTHER PUBLICATIONS

Caster et al., Unpublished U.S. Appl. No. 16/602,840, filed Dec. 10, 2019, titled "Blueberry Plant Variety Named DrisBlueTwentyOne".
Caster et al., Unpublished U.S. Appl. No. 16/350,021, filed Sep. 13, 2018, titled "Blueberry Plant Variety Named 'DrisBlueSeventeen'".
Caster et al. "Unpublished U.S. Appl. No. 16/501,199, filed Mar. 5, 2019, titled "Blueberry Plant Variety Named 'DrisBlueTwenty'"".
Mowrey et al., Unpublished U.S. Appl. No. 16/350,020, filed Sep. 13, 2018, titled "Blueberry Plant Variety Named 'DrisBlueSixteen'".
Mowrey et al., Unpublished U.S. Appl. No. 16/350,226, filed Oct. 16, 2018, titled "Blueberry Plant Variety Named 'DrisBlueNineteen'".
Mowrey et al., Unpublished U.S. Appl. No. 16/873,056, filed Jan. 23, 2020, titled "Blueberry Plant Variety Named DrisBlueTwentyTwo".

*Primary Examiner* — Susan McCormick Ewoldt
(74) *Attorney, Agent, or Firm* — Morrison & Foerster LLP

(57) ABSTRACT

A new and distinct variety of blueberry plant named 'DrisBlueTwentyThree', particularly selected for its pleasant minty sweet fruit flavor, juicy crisp fruit texture, large fruit size, strong evergreening ability of the plant, and early production, is disclosed.

6 Drawing Sheets

Latin name:
Botanical classification: *Vaccinium corymbosum* L.
Varietal denomination: The varietal denomination of the claimed variety of blueberry plant is 'DrisBlueTwentyThree'.

BACKGROUND OF THE INVENTION

Blueberry plants are perennial flowering plants with indigo-colored berries from the section Cyanococcus within the genus *Vaccinium*. Many commercially sold species with English common names, including blueberry, are currently classified in section Cyanococcus of the genus *Vaccinium* and come predominantly from North America. Many North American native species of blueberries are grown commercially in the Southern Hemisphere in Australia, New Zealand, and South American nations.

*Vaccinium corymbosum*, the northern highbush blueberry, is a North American species of blueberry which has become a food crop of significant economic importance. It is native to eastern Canada and the eastern and southern United States, from Ontario east to Nova Scotia and south as far as Florida and eastern Texas. It has been naturalized in Europe, Japan, New Zealand, and the Pacific Northwest of North America. Other common names include blue huckleberry, tall huckleberry, swamp huckleberry, high blueberry, and swamp blueberry.

Blueberries are usually erect, prostrate shrubs that can vary in size from approximately four inches to approximately 13 feet in height. In the commercial production of blueberries, the smaller species are known as "lowbush blueberries", while the larger species are known as "highbush blueberries".

Blueberry bushes typically bear fruit in the middle of the growing season. However, fruiting times can be affected by local conditions such as altitude and latitude. As such, peak crop can vary from May to August in the northern hemisphere, depending upon these conditions.

Blueberries are a popular fruit that is typically consumed as fresh fruit, individually quick frozen (IQF) fruit, or in prepared foods, such as purées, juices, jellies, jams, baked goods, snack foods, and cereals.

Blueberry is an important and valuable fruit crop. Accordingly, there is a need for new varieties of blueberry plant. In particular, there is a need for improved varieties of blueberry plant that are stable, high yielding, and agronomically sound.

SUMMARY OF THE INVENTION

In order to meet these needs, the present invention is directed to an improved variety of blueberry plant. In particular, the invention relates to a new and distinct variety of blueberry plant (*Vaccinium corymbosum* L.), which has been denominated as 'DrisBlueTwentyThree'.

Blueberry plant variety 'DrisBlueTwentyThree' was discovered in Hillsborough County, Fla. in April of 2013 and originated from a cross between the proprietary female parent blueberry plant '196H 3' (unpatented) and the proprietary male parent blueberry plant '75J301' (unpatented). The original seedling of the new variety was first asexually propagated via softwood cuttings in Santa Cruz County, Calif. in July of 2013.

'DrisBlueTwentyThree' was subsequently asexually propagated via softwood cuttings and tissue culture and underwent further testing in Ventura County, Calif. for five years (2014 to 2019). The present blueberry variety has been found to be stable and reproduce true to type through successive asexual propagations via softwood cuttings and tissue culture.

'DrisBlueTwentyThree' exhibits the following distinguishing characteristics when grown under normal horticultural practices in Ventura County, Calif.:

1. Ovate leaf shape;
2. Straight fruit sepals;
3. High sweetness of fruit; and
4. Fruiting on one-year-old and current season's shoots.

'DrisBlueTwentyThree' was selected for its pleasant minty sweet fruit flavor, juicy crisp fruit texture, large fruit size, strong evergreening ability of the plant, and early production.

BRIEF DESCRIPTION OF THE DRAWINGS

This new blueberry plant variety is illustrated by the accompanying photograph. The colors shown are as true as can be reasonably obtained by conventional photographic procedures. The photograph is of plants that are four and a half years old, unless otherwise specified.

DETAILED BOTANICAL DESCRIPTION

Figure 1:
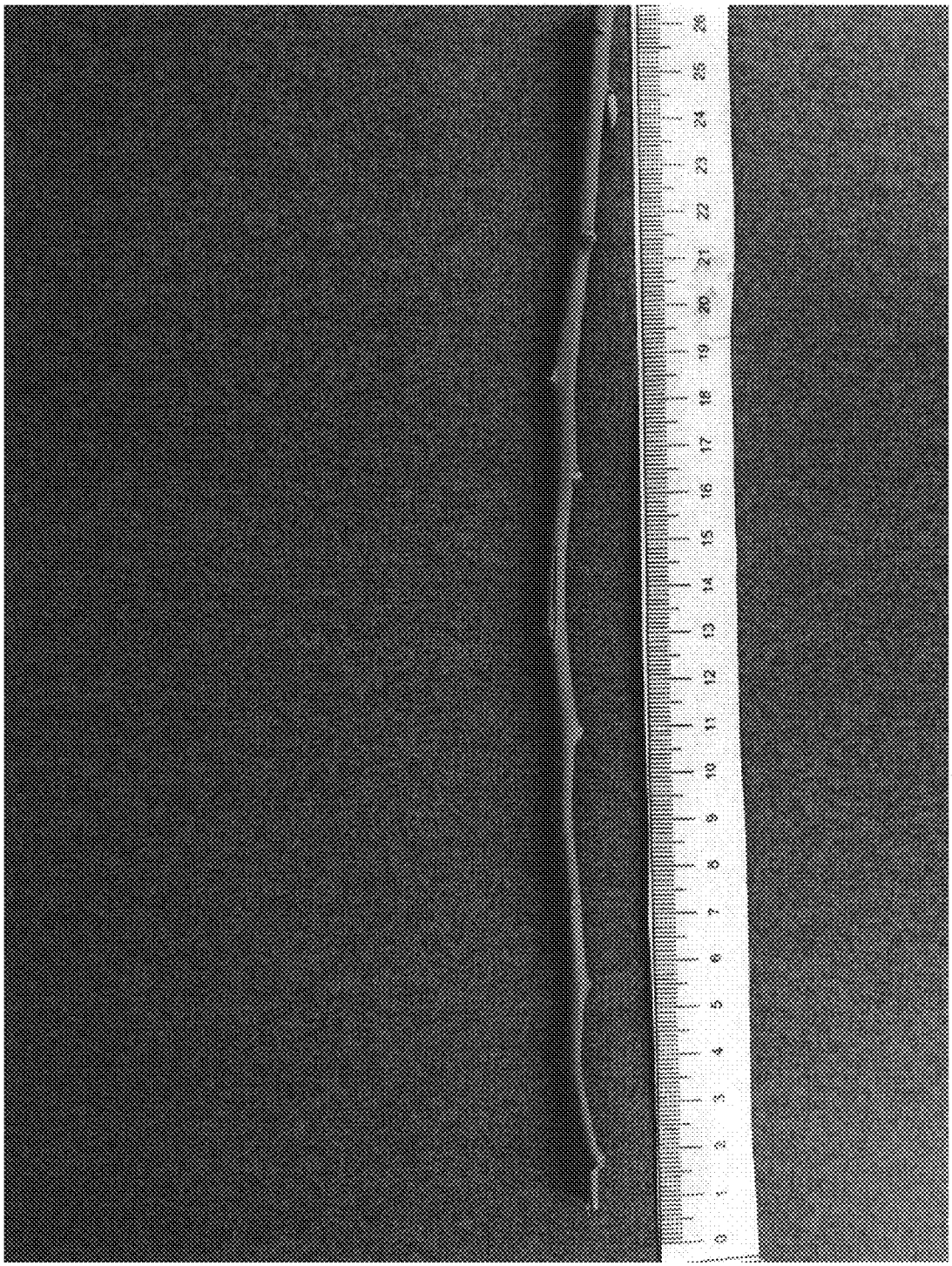
FIG. 1 illustrates a section of a cane of variety 'DrisBlueTwentyThree'.
Figure 2:
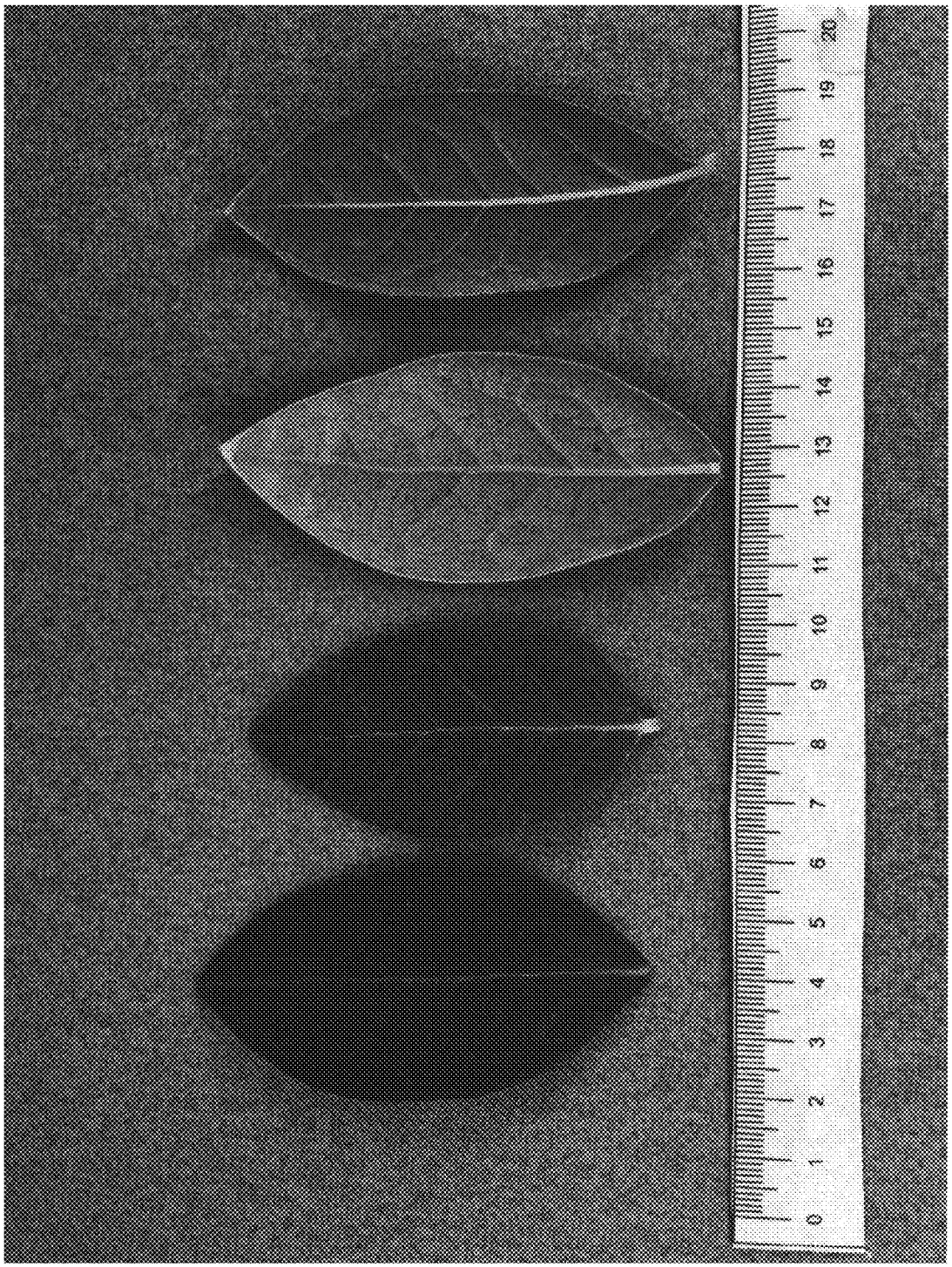
FIG. 2 illustrates leaves of variety 'DrisBlueTwentyThree'. The two leaves on the left show the upper leaf surfaces and the two leaves on the right show the lower leaf surfaces.
Figure 3:
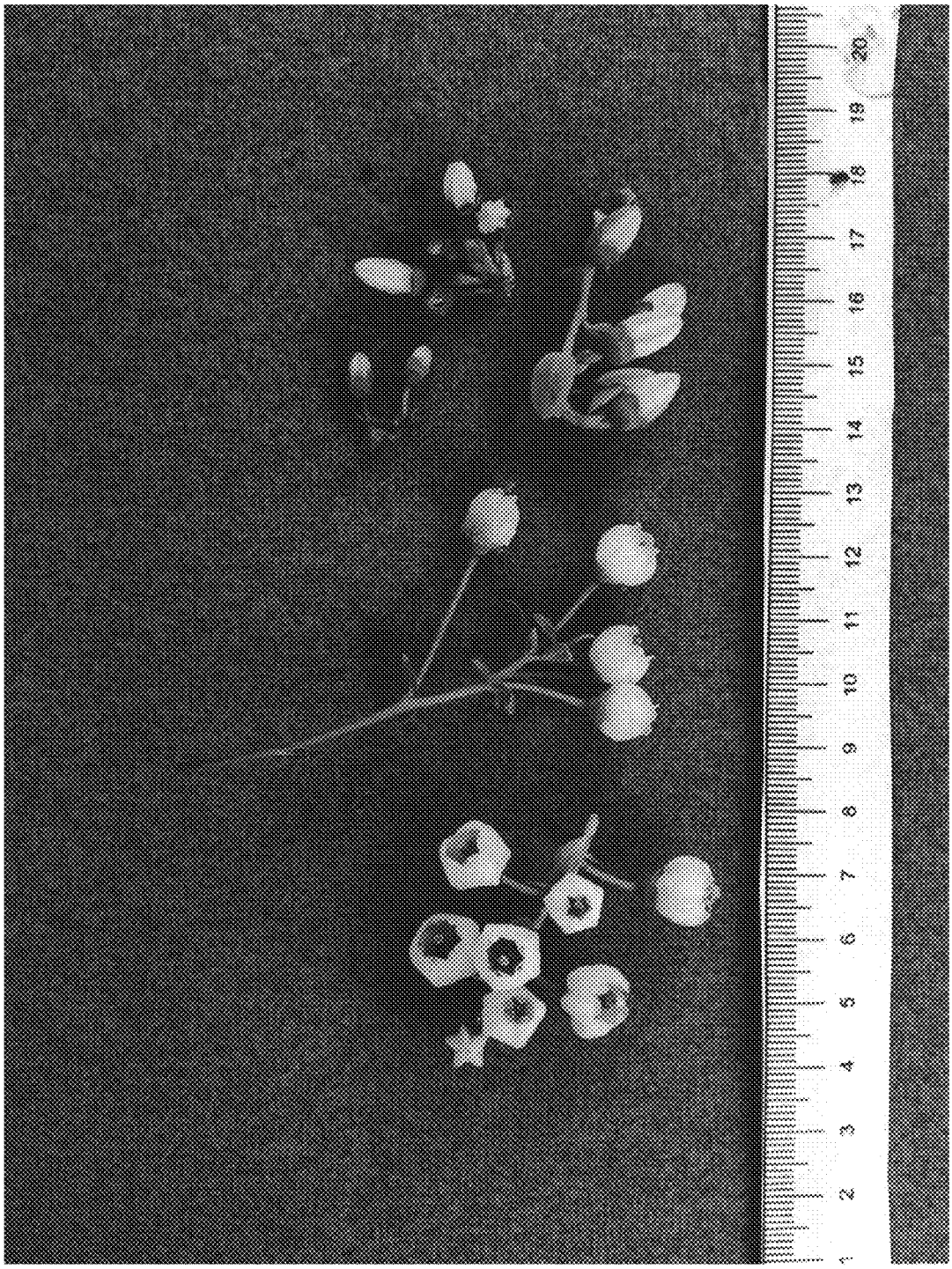
FIG. 3 illustrates clusters of flowers of variety 'DrisBlueTwentyThree' at various developmental stages.
Figure 4:
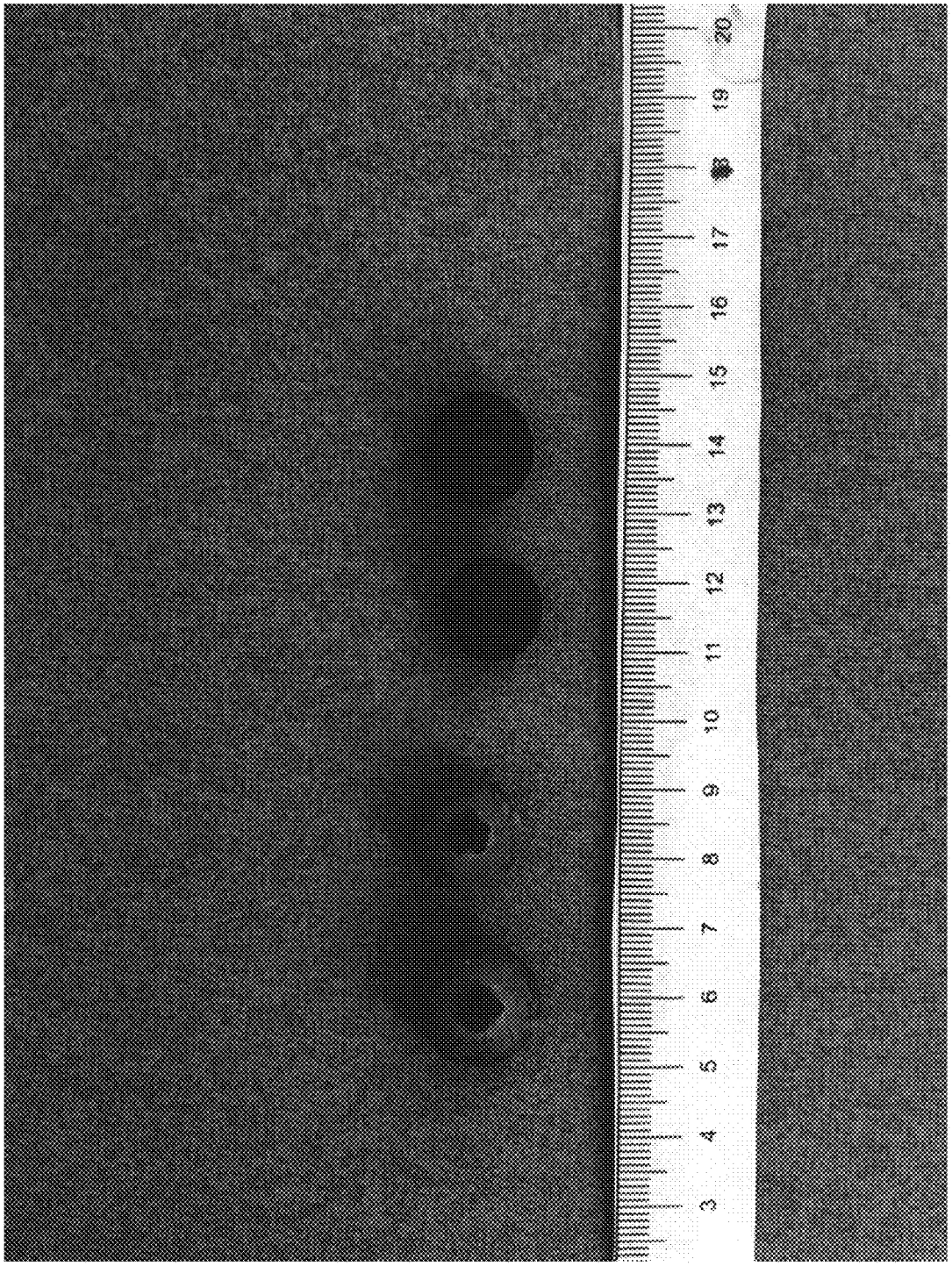
FIG. 4 illustrates whole fruit of variety 'DrisBlueTwentyThree'. The two fruit on the left have bloom on them and show the top view (calyx basin) of the whole fruit, whereas the two fruit on the right have bloom removed and show the bottom view (fruit-pedicel junction) of the whole fruit.
Figure 5:
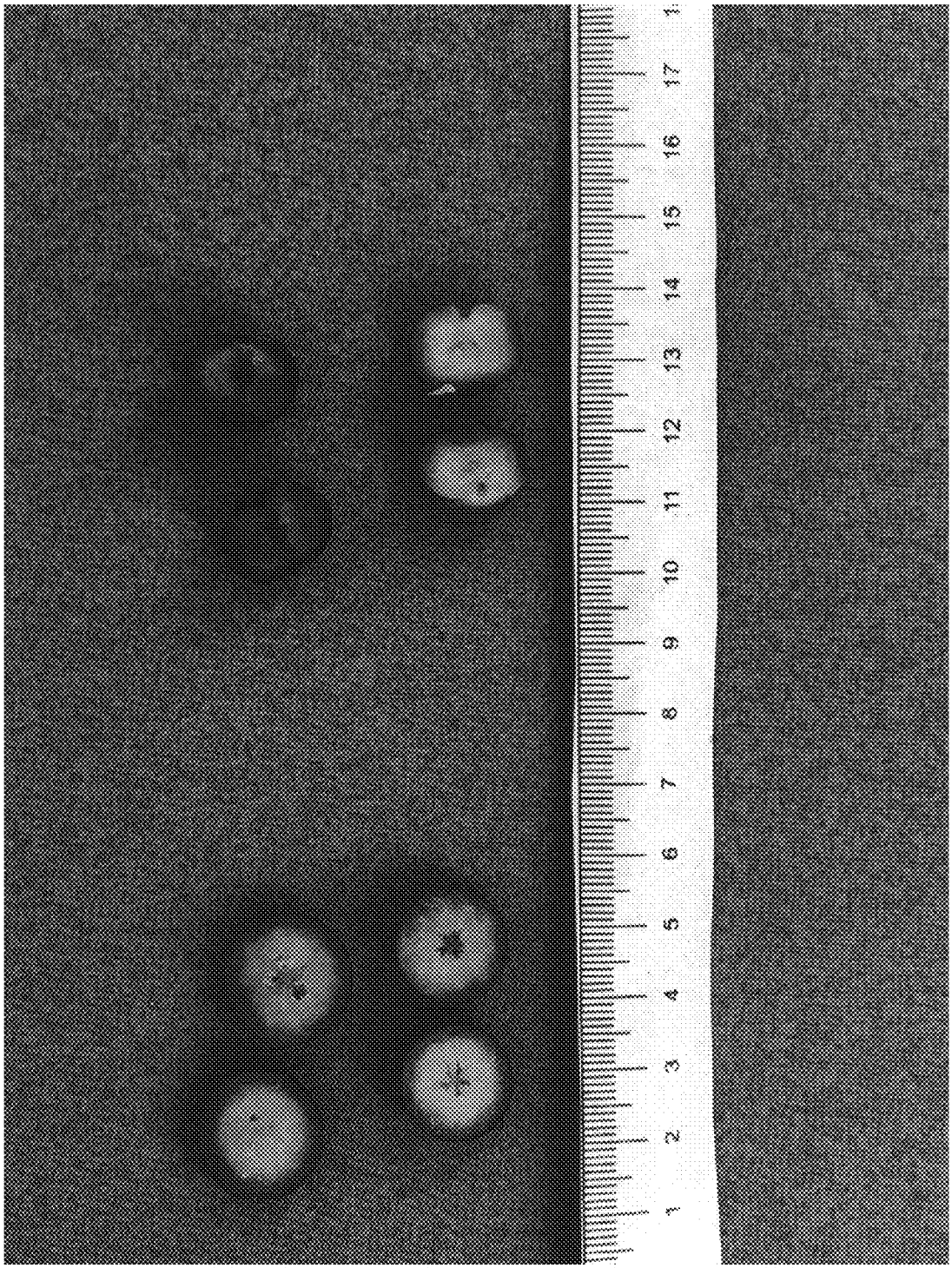
FIG. 5 illustrates the cross-sections (two columns of fruit on the left) and longitudinal sections (two columns of fruit on the right) of fruit of variety 'DrisBlueTwentyThree'.
Figure 6:
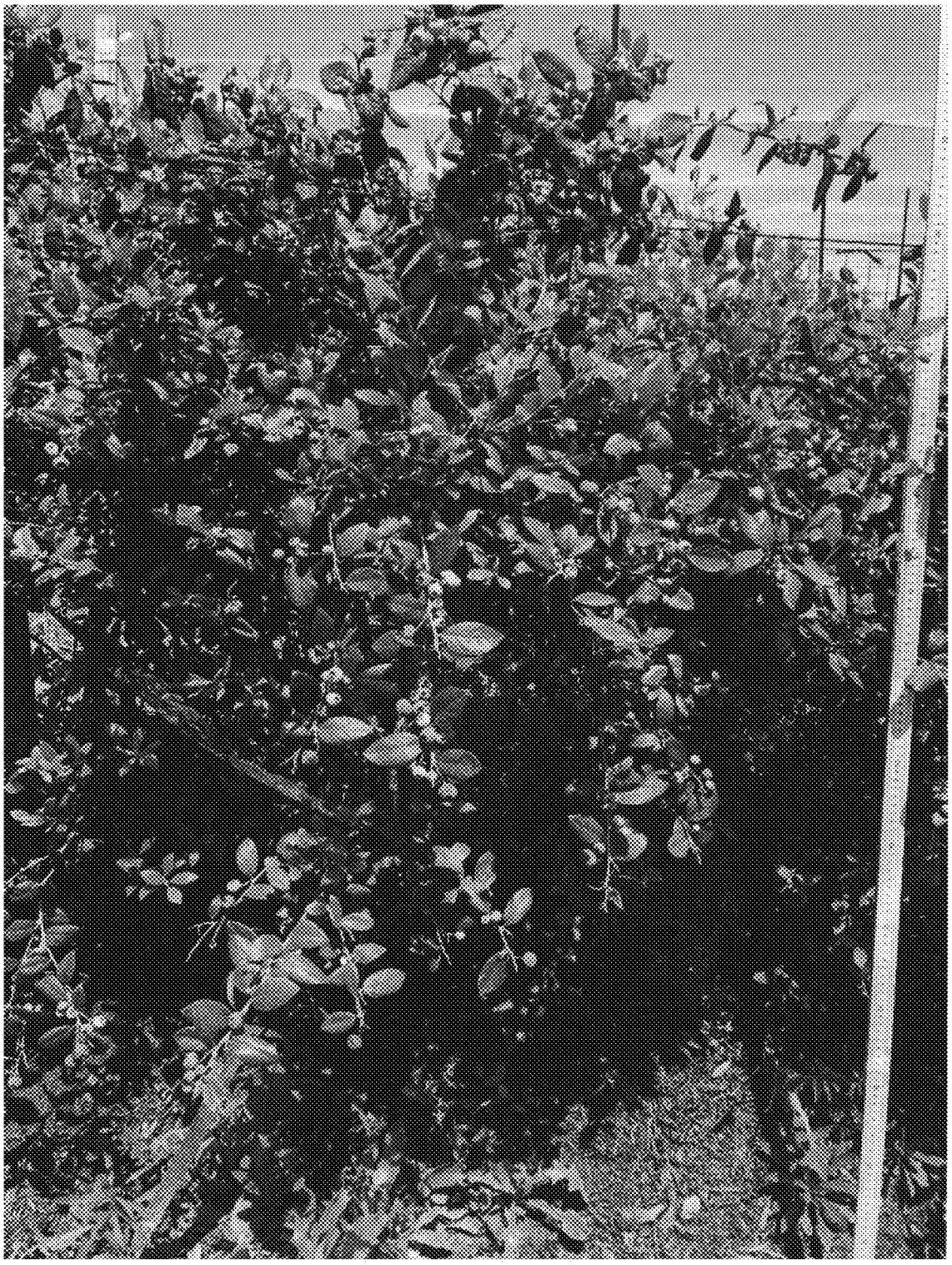
FIG. 6 illustrates plants of variety 'DrisBlueTwentyThree'.

The following description sets forth the distinctive characteristics of 'DrisBlueTwentyThree'. The data which define these characteristics is based on observations taken in Ventura County, Calif. from 2014 to 2019. This description is in accordance with UPOV terminology. Color designations, color descriptions, and other phenotypical descriptions may deviate from the stated values and descriptions depending upon variation in environmental, seasonal, climatic and cultural conditions. 'DrisBlueTwentyThree' has not been observed under all possible environmental conditions. Unless noted otherwise, the botanical description of 'DrisBlueTwentyThree' was taken from plants that were four and a half years old. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* $2^{nd}$ edition by James G. Harris and Melinda Woolf Harris, unless where otherwise defined.

Classification:

*Family.*—Ericaceae.
*Botanical.*—*Vaccinium corymbosum* L.
*Common name.*—Blueberry.
*Variety name.*—'DrisBlueTwentyThree'.

Parentage:

*Female parent.*—The proprietary blueberry plant '196H 3' (unpatented).
*Male parent.*—The proprietary blueberry plant '75J301' (unpatented).

Plant:

*Height.*—137.7 cm.
*Width.*—118.9 cm.
*Length/width ratio.*—1.2.
*Vigor.*—Medium.
*Growth habit.*—Semi-upright.
*One-year-old canes* (*young canes*).—Length: 78 cm. Diameter at the base: 7 mm. Diameter at the tip: 2 mm. Internode length on the upper half: 23.8 mm. Color: RHS 142A (Strong yellow-green).
*Five-year-old canes* (*mature canes*).—Length: 75 cm. Diameter at the base: 19 mm. Diameter at the tip: 2 mm.

Leaves:

*Length.*—63.5 mm.
*Width.*—33.2 mm.
*Length/width ratio.*—1.9.
*Internode length.*—19.95 mm.
*Shape.*—Ovate.
*Margin.*—Entire.
*Color on upper side.*—RHS NN137A (Greyish olive green).
*Color of lower side.*—RHS 147B (Moderate yellow-green).
*Shape of the leaf apex.*—Acute.
*Shape of the leaf base.*—Attenuate.
*Leaf arrangement.*—Alternate.
*Petiole.*—Length: 4.9 mm. Diameter: 1.97 mm. Color: RHS 145A (Strong yellow-green).

Flowers:

*Inflorescence length.*—41.9 mm.

*Flower length (excluding pedicel).*—10.41 mm.

*Flower diameter.*—7.81 mm.

*Flower length/width ratio.*—1.3.

*Flower bud.*—Length: 8 mm. Width: 4 mm. Number of flowers per bud: 4. Color with anthocyanin present: RHS 155A (Pale yellow-green).

*Flower pedicel.*—Length: 7.78 mm. Diameter: 1.14 mm.

*Corolla.*—Shape: Urceolate. Anthocyanin coloration of corolla tube: Absent or very weak. Color of corolla tube: RHS 155A (Pale yellow-green). Ridges on corolla tube: Absent. Petal width (ridge to ridge): 6.05 mm. Diameter of corolla aperture: 6.16 mm.

*Reproductive organs.*—Style length (including stigma): 9.24 mm.

*Flowering interval on one-year-old shoot.*—December to April.

*Flowering interval on current season's shoot.*—December to April.

Fruit:

Length.—11.06 mm.

*Diameter.*—14.11 mm.

*Length/width ratio.*—0.8.

*Weight.*—2.0 grams.

*Shape in longitudinal section.*—Oblate.

*Attitude of sepals.*—Straight.

*Calyx basin.*—Diameter: 6.00 mm. Depth (including sepals): 2.52 mm. Diameter/depth ratio: 2.4.

*Number of berries per cluster.*—5.

*Fruit cluster peduncle length.*—19.59 mm.

*Diameter of fruit pedicel.*—1.56 mm.

*Color of pedicel.*—RHS 145A (Strong yellow-green).

*Color of unripe fruit.*—RHS 142C (Light yellow-green).

*Color of fruit without bloom on mature fruit.*—RHS 203D (Blueish black).

*Fruit flesh color.*—RHS 157B (Pale yellow-green).

*Fruit firmness.*—Medium.

*Fruit sweetness.*—High.

*Fruit acidity.*—Low.

*Fruiting type.*—On one-year-old and current season's shoots.

*Ripening interval on one-year-old shoot.*—February to June.

*Ripening interval on current season's shoot.*—February to June.

*Yield.*—25 kg to 35 kg of fruit per acre per season from 24- to 36-month old plants when grown at Oxnard, Calif.

Resistance to abiotic stress, pests, and diseases:

*Blueberry bud mite (Acalitus vaccinii).*—Moderately resistant.

*Spotted-wing drosophila (drosophila suzitkii).*—Moderately susceptible.

COMPARISONS TO PARENTAL AND COMMERCIAL BLUEBERRY VARIETIES

'DrisBlueTwentyThree' differs from the proprietary female parent '196H 3' (unpatented) in that fruit of 'DrisBlueTwentyThree' have better firmness, color, flavor, and shelf life than fruit of '196H 3'. Additionally, plants of 'DrisBlueTwentyThree' have an earlier fruit timing and are more productive than plants of '196H 3'.

'DrisBlueTwentyThree' differs from the proprietary male parent '75J301' (unpatented) in that fruit of 'DrisBlueTwentyThree' have better flavor than fruit of '75J301'. Further, unlike '75J301', no fruit shriveling has been observed for 'DrisBlueTwentyThree'. Additionally, plants of 'DrisBlueTwentyThree' have an earlier fruit timing and are more productive than plants of '75J301'.

'DrisBlueTwentyThree' differs from the commercial blueberry plant variety 'DrisBlueSeven' (U.S. Plant Pat. No. 24,605) in that 'DrisBlueTwentyThree' has an ovate leaf shape, straight fruit sepals, medium fruit firmness, and high fruit sweetness, whereas 'DrisBlueSeven' has an elliptic leaf shape, incurving and straight fruit sepals, very firm fruit firmness, and medium fruit sweetness.

'DrisBlueTwentyThree' differs from the commercial blueberry plant variety 'DrisBlueFour' (U.S. Plant Pat. No. 24,407) in that 'DrisBlueTwentyThree' has an ovate leaf shape, straight fruit sepals, high fruit sweetness, and a fruiting type of both on one-year-old and current season's shoots, whereas 'DrisBlueFour' has an elliptic leaf shape, incurving and straight fruit sepals, medium fruit sweetness, and a fruiting type of only on one-year-old shoots.

What is claimed is:

1. A new and distinct variety of blueberry plant designated 'DrisBlueTwentyThree' as shown and described herein.

* * * * *